United States Patent
Werenskiold

(12) 
(10) Patent No.: US 6,399,748 B1
(45) Date of Patent: Jun. 4, 2002

(54) IN-VITRO METHOD FOR PROGNOSTICATING THE ILLNESS DEVELOPMENT OF PATIENTS WITH CARCINOMA OF THE BREAST AND/OR FOR DIAGNOSING CARCINOMA OF THE BREAST

(75) Inventor: Anne Katrin Werenskiold, Munich (DE)

(73) Assignee: GSF-Forschungszentrum fur Umwelt und Gesundheit, GmbH, Neuherberg (DE)

( * ) Notice: Subject to any disclaimer, the term of this patent is extended or adjusted under 35 U.S.C. 154(b) by 0 days.

(21) Appl. No.: 09/399,646

(22) Filed: Sep. 21, 1999

Related U.S. Application Data

(63) Continuation of application No. PCT/EP98/01627, filed on Mar. 20, 1998.

(30) Foreign Application Priority Data

Mar. 21, 1997 (DE) .......................................... 197 11 932

(51) Int. Cl.$^7$ .............................................. C07K 16/00

(52) U.S. Cl. .................. 530/388.21; 530/350; 530/380; 530/385; 530/386; 530/387.1; 530/387.7; 530/388.1; 530/388.2; 530/389.1; 530/389.7; 435/4; 435/6; 435/7.1; 435/7.21; 435/7.23; 435/7.9; 435/7.92; 435/7.94; 436/63; 436/64; 436/512

(58) Field of Search ................................. 530/350, 380, 530/385, 386, 387.1, 387.7, 388.1, 388.2, 389.1, 389.7, 388.21; 435/4, 6, 7.1, 7.21, 7.23, 7.9, 7.92, 7.94; 436/63, 64, 512

(56) References Cited

PUBLICATIONS

Harlow and Lane. Antibodies: A Laboratory Manual. Cold Spring Harbor Laboratory. 1988.*
Chemical Abstracts, vol. 118, No. 19, Abstract No. 188980 (May 1993).
Chemical Abstracts, vol. 116, No. 17, Abstract No. 171919 (Apr. 1992).
Chemical Abstracts, vol. 112, No. 17, Abstract No. 152789 (Apr. 1990).
Biological Abstracts, vol. 98, Abstract No. 107727 (1998).
Werenskiold et al., 1996, Cancer Detection and Prevention 20:5.
Danescu and Werenskiold, 1995, FEBS Lett. 367:889–92.
Gayle et al., 1996, J. Biol. Chem. 271:5784–5789.
Klemenz et al., 1989, Proc. Natl. Acad. Sci. USA 86:5708–5712.
Röβler et al., 1993, Oncogene 8:609–617.
Röβler et al., 1995, Dev. Biol. 168:86–97.
Rupp et al., 1995, Biochem. Biophys. Res. Com. 216:595–601.
Roessler et al., 1995, E. J. Pathol. 1 file 952–03.
Thomassen et al., 1995, Cell Growth Differ. 6:178–184.
Werenskiold, 1992, Eur. J. Biochem. 204:1041–1047.
Werenskiold et al., 1989, Mol. Cell Biopl. 9:5207–5214.

* cited by examiner

*Primary Examiner*—Anthony C. Caputa
*Assistant Examiner*—Alana M. Harris
(74) *Attorney, Agent, or Firm*—Akin, Gump, Strauss, Hauer & Feld, L.L.P.

(57) ABSTRACT

The present invention is directed to a method of prognosticating the illness development of patients with carcinoma of the breast and/or for diagnosing carcinoma of the breast, the method comprising a qualitative determination of T1 protein and/or T1-mRNA in a sample material obtained from the patient. The invention further pertains to kits for performing the methods according to the invention.

10 Claims, 5 Drawing Sheets

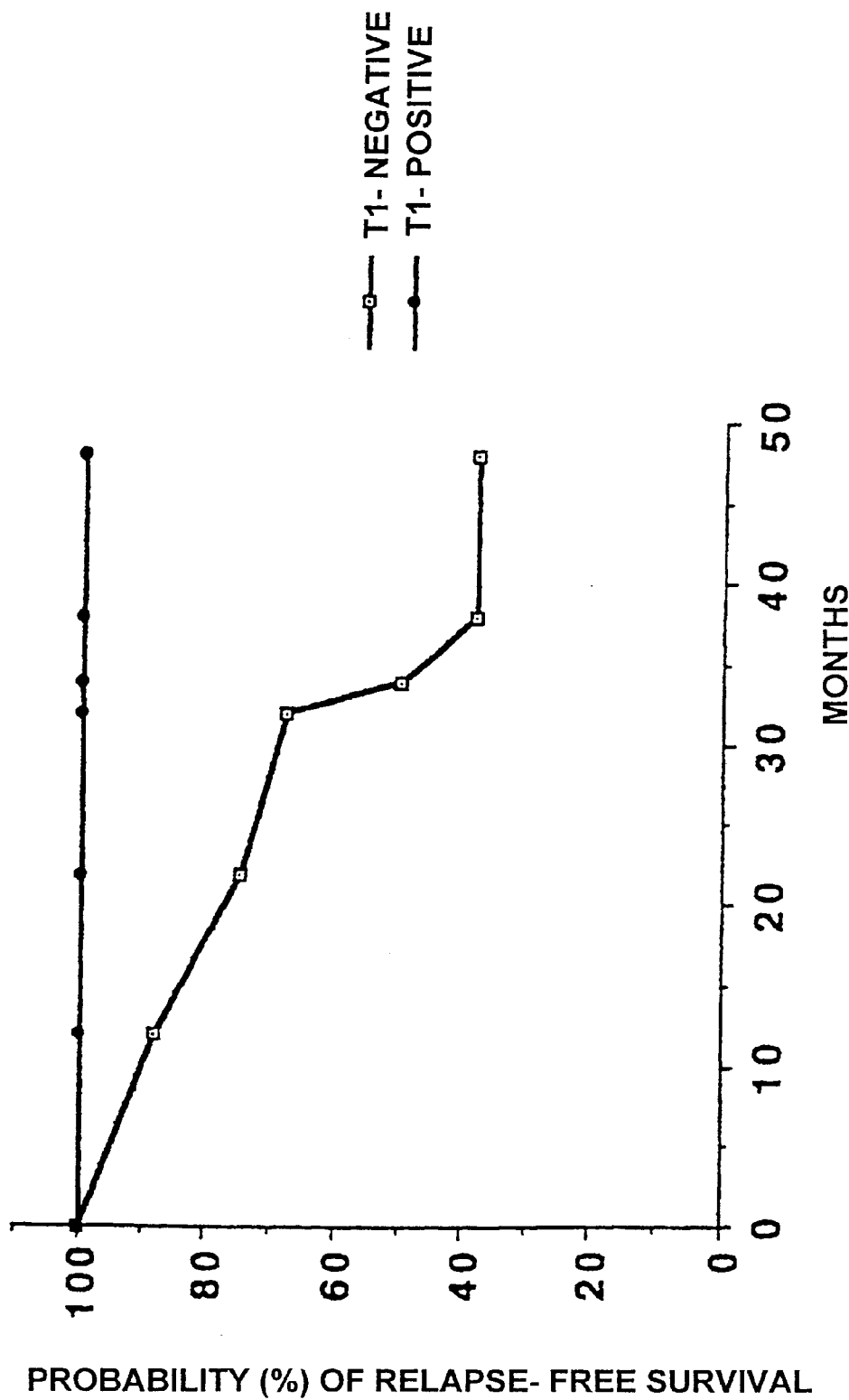
FIG. 3: METASTASIS IN NODAL-NEGATIVE PATIENTS

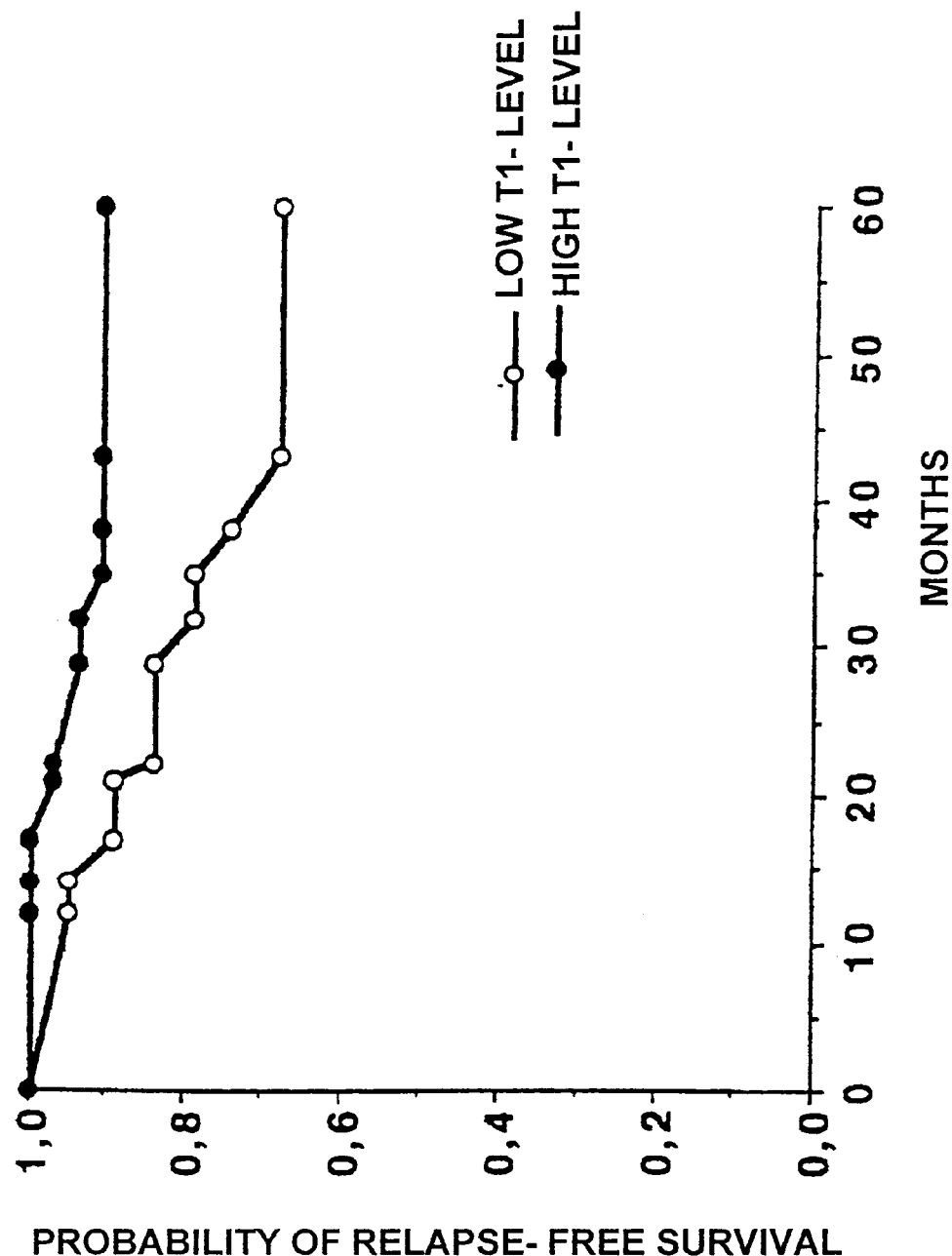

IN-VITRO METHOD FOR PROGNOSTICATING THE ILLNESS DEVELOPMENT OF PATIENTS WITH CARCINOMA OF THE BREAST AND/OR FOR DIAGNOSING CARCINOMA OF THE BREAST

CROSS-REFERENCE TO RELATED APPLICATIONS

This application is a continuation of International Application PCT/EP98/01627, filed on Mar. 20, 1998.

The present invention relates to an in-vitro method for prognosticating the illness development of patients with carcinoma of the breast and/or for diagnosing carcinoma of the breast, to kits suitable for performing said method, and to the use of T1-specific antibodies or fragments thereof or of T1-specific oligonucleotides for determining T1 protein or T1-mRNA in patients with carcinoma of the breast.

Carcinomas of the breast, in particular invasive carcinomas of the breast, are malign tumors with an extremely different clinical development that could so far not be predicted. Invasive carcinoma of the breast is the most frequently observed malign tumor in women; on the statistical average, every 16th woman suffers therefrom. In the case of an existing carcinoma of the breast, the breast tumor is first of all removed as the primary therapeutic measure. Especially the nodal state, but also tumor size, histological type, degree of differentiation and hormone receptor condition are nowadays regarded as important parameters for prognosis and further therapeutic planning. Emphasis is however placed on the evaluation of the state of the axillary lymph node. For instance with patients suffering from lymph node disease in the axillary region (nodal-positive, N(+)) already at the time of tumor diagnosis or surgery, a chemotherapy is normally carried out immediately, optionally supported by an additional radiation therapy. In general, patients with a negative axillary lymph node state (nodal-negative, N(0)) have a better chance and, therefore, are in general not subjected to a chemotherapeutic or radiation-therapeutic aftertreatment. Statistically, however, up to 30% of the patients classified as N(0) suffer from a relapse (Yan 1992). Such a high rate of relapse demonstrates that the factors of prognosis that have so far been known describe the illness development in a very incomplete manner only.

In recent years a great number of molecules were tested as to their possible use as prognosis factors for carcinoma of the breast (for the purpose of survey: Schmitt et al., 1994; Hoskins and Weber 1995), e.g. (proto)oncogenes such as c-erbB-2 (Allred et al., 1992, Archer et al., 1995), the tumor suppressor gene p53 (Barnes et al., 1993, Lipponen et al., 1993), the urokinase-type plasminogen activator uPA (Jaenicke et al., 1993; Wilhelm et al., 1994), the adhesion molecule E-cadherin (Rasbridge et al., 1993; Graff et al., 1995) and the cytoskeleton protein vimentin (Sommers et al., 1992). The vimentin synthesis correlates with the invasive growth of breast-carcinoma cell lines in vitro (Thompson et al., 1991) and partly with rapidly growing invasive ductal breast carcinomas having a poor prognosis in vivo (Domagala et al., 1990). Furthermore, possible factors of prognosis are formed by cytometrically determined morphometric features and texture features and also by DNA parameters (Auer et al., 1994).

However, none of the above-mentioned factors permits a sufficiently reliable prognosis of the further illness development after removal of the breast carcinoma.

It is therefore the object of the present invention to provide a method which allows for a sufficiently reliable prognosis of the further illness development in patients with carcinoma of the breast.

According to the invention this object is achieved by an in-vitro method for prognosticating the illness development of patients with carcinoma of the breast and/or for diagnosing carcinoma of the breast, which method comprises the qualitative or quantitative determination of T1 protein and/or T1-mRNA in sample material obtained from patients.

The T1 protein is an extracellular, soluble glycoprotein of 60–70 kDa (Werenskiold, 1992) with homology to members of the immunoglobulin superfamily, in particular the carcinoma-embryonal antigen (Klemenz et al., 1989).

The molecule was identified in an analysis of the former effects of oncoproteins ($p21^{ras}$ and $p39^{v-mos}$) on the gene expression in fibroblasts (Werenskiold et al., 1989). In the mouse there is a synthesis of the T1 protein in embryonal tissues only; it cannot be detected in the adult animal (Rößler et al., 1995 a,b). The function of the T1 protein has not been completely darified yet, but the isolation of a second membrane-bound variant of the molecule (T1-M) points to a function as a cytokine receptor. The membrane-bound T1-M protein is very similar to the IL-1 receptor type 1, but has no affinity to the cytokines IL-1 α and β (Rößler et al, 1995 b; Danescu and Werenskiold, 1995) or IL-1 ra (Gayle et al., 1996). T1-M is a novel mast cell-specific cytokine receptor (Rößler et al., 1995 b; Thomassen et al., 1995). The oncogene-inducible soluble variant of the T1 protein is a shortened form of said receptor and corresponds to the ligand-binding domain thereof. Recombinantly produced, soluble T1 from the mouse (Rupp et al., 1995) blocks the growth of mast cells.

So far, in breast carcinomas of the mouse, an overexpression of the soluble T1 protein has exclusively been observed in invasively growing, poorly differentiated tumors. Both the tumor stroma and the anaplastic tumor cells synthetize T1. In-situ hybridizations demonstrate an increased expression of T1 in tumor cells on the periphery of tumor cell complexes and, possibly induced by the tumor cells, in the stroma cells directly adjacent thereto (Rößler et al, 1993). The induction of the T1 expression in the tumor cells correlates with the phenotypic transformation thereof and is accompanied by a loss in the E-cadherin and cytokeratin production. It is controlled by an AP1-dependent promoter of the T1 gene which is only active in non-hemopoietic (e.g. fibroblastic) cells (Thomassen et al., 1995). During phenotypic transformation of the epithelial tumor cells the induction of T1 is distinctly performed prior to that of the also AP1-dependent, mesenchymal cytoskeleton protein vimentin and therefore forms an early marker for the transformation process.

Surprisingly enough, it has now been found that the presence or absence of a T1 transcription or expression provides information about the future illness development, in particular information about the probability of the occurrence of a relapse or of the development or growth of metastases. As will be explained in detail in the examples, a high T1 value surprisingly correlates with a positive prognosis in patients with an N(0) nodal state whereas a high T1 protein or T1-mRNA level means a negative prognosis in patients with an N(+) nodal state.

In a preferred embodiment the T1 protein and/or the T1-mRNA is determined in a tumor tissue sample of the patient. To this end tissue sections are e.g. made and fixed in accordance with standard methods and are subsequently subjected either to an immunoassay for detecting an existing T1 protein or to hybridization with oligonucleotides, which are or can be labeled, or with DNA fragments. Total RNA or poly(A)⁺-mRNA can optionally be isolated from the tumor tissue according to standard methods and, for example after a gel-electrophoretic separation or after fixation to a solid matrix, the total RNA or poly(A)⁺-mRNA can then be determined again by hybridization with an oligonucleotide which is or can be labeled.

T1 protein can be detected not only in the tumor tissue itself, but also in various body fluids of the patients afflicted. In a preferred embodiment the method of the invention is carried out with a blood or serum sample:

There are a number of methods for determining T1-mRNA. As has already been pointed out above, it is possible, on the one hand, to detect T1-mRNA in situ or in corresponding RNA or mRNA preparations by hybridization with a corresponding oligonucleotide probe or a DNA fragment. The oligonucleotide probe or the DNA fragment itself can produce a measurable signal, i.e. it may be radioactively labeled, or can be capable of producing a signal by interacting with other molecules. For an improved evaluation of the corresponding tests the signal should be amplified in most cases. The target nucleic acid to be detected is normally amplified for this purpose.

For the amplification of the target sequence, i.e. T1-mRNA, by the PCR method (polymerase chain reaction) a cDNA copy is first of all made according to known methods. Said cDNA copy is then subjected to a PCR method. The sequence of the human T1 gene is already known in part (Tominaga et al., 1992); the selection of suitable oligonucleotides for performing the reverse transcription and the PCR method is thus within the scope of expert skill. An example of a suitable oligonucleotide is the oligonucleotide with the sequence 5'-CTT TGA TCA CCT GAA CTT TCT CTA GCA-3' (SEQ ID NO:1) or a fragment thereof. A further suitable primer is the antisense primer 5'-AGT TTT CGG TTG TTG GTG CAT TTC-3' (SEQ ID NO:2) or a suitable fragment thereof. Preferred primers derive from the 3'-untranslated region and/or the region of the exons 8 and 9. Primers from said regions have the advantage that they only hybridize with the RNA coding for the tumor-associated T1-S protein, but not with the T1-M-mRNA obtained by alternative splicing. One of the specific primers, sense or antisense, can optionally be replaced by a commercially available random primer. A number of further processes by which the target nucleic acids can be amplified have become known in the prior art in the meantime. Reference is here e.g. made to the Q-NASBA method in which the mRNA existing in the sample is amplified by the concerted action of reverse transcriptase, RNase H and T7 polymerase (Kievits et al., 1991). A further possibility is the detection of DNA obtained after reverse transcription through the so-called "strand displacement amplification" (SDA) (Walker et al., 1996, and the literature cited therein). One skilled in the art is also aware of a number of further methods which can also be used for detecting or determining T1-mRNA.

The amplification products formed are detected in a manner known to one skilled in the art. For instance, the DNA synthetized with the PCR method can be made visible by the incorporation of digoxigenin-containing nucleotides and subsequent reaction with enzyme-conjugated anti-digoxigenin antibodies. Any enzyme capable of producing a signal can be conjugated with the anti-digoxigenin antibody, for instance alkaline phosphatase, acid phosphatase, peroxidase, β-D-galactosidase, glucose oxidase and horseradish peroxidase. In response to the substrate used, the T1-mRNA can be detected quantitatively, e.g. by measuring the absorption or fluoresence of soluble products, or at least qualitatively.

For instance, the anti-digoxigenin antibody conjugated with alkaline phosphatase, which is obtainable from Boehringer Mannheim, is well suited for determining the existing T1-mRNA. One skilled in the art is aware that there are still further possibilities of detecting amplified nucleic acids, e.g. by incorporation of biotin-labeled nucleotides and subsequent reaction of the products with avidin- or streptavidin-conjugated enzymes which make it possible to produce a signal. Finally, such an enzyme may also be coupled to a third oligonucleotide which is complementary to a segment of a strand of one of the amplified nucleic acids.

The following table furnishes information about the normally used enzymes and about chromogenic substrates to be possibly used in combination with said enzymes.

TABLE 1

| Enzymes | Chromogens |
|---|---|
| 1. alkaline phosphatase and acid phosphatase | 4-methyl umbelliferyl phosphate (*), bis(4-methyl umbelliferyl phosphate), (*) 3-0-methyl fluorescein, flavone-3-diphosphate triammonium salt (*), p-nitrophenyl phosphate disodium salt |
| 2. peroxidase | tyramine hydrochloride (*), 3-p-(hydroxyphenyl) propionic acid (*), p-hydroxyphenethyl alcohol (*), 2,2'-azino-di-3-ethyl benzothiazoline sulfonic add (ABTS), ortho-phenylene diamine dihydrochloride, o-dianisidine, 5-aminosalicylic acid, p-ucresol (*), 3,3'-dimethyl oxybenzidine, 3-methyl-2-benzothiazoline hydrazone, tetramethyl benzidine |
| 3. horse-radish peroxidase | $H_2O_2$ + diammonium benzidine $K_2O_2$ + tetramethyl benzidine |
| 4. β-D-galactosidase | o-nitrophenyl-β-D-galactopyranoside, 4-methyl umbelliferyl-β-D-galactoside |
| 5. glucose oxidase | ABTS, glucose and thiazolyl blue | note:
(*): fluorescent product

After gel electrophoresis of the reaction mixture the detection of the amplification products may be performed in the gel, but also in solution or after binding to a solid matrix. A number of systems are presently available on the market, which serve the detection of amplified DNA and can be tailored to the requirements regarding the detection of T1-mRNA.

While the above-mentioned methods involve the reverse transcription and/or amplification of the nucleic acid to be detected (in the present case T1-mRNA), thereby permitting a detection of even very slight amounts of T1-mRNA, other methods are based on the detection of the molecules by amplification of the signal. An example thereof is the bDNA method (Pachl et al., 1994) in which the nucleic acid to be detected is coupled via hybridization with an oligonucleotide to a solid matrix, via a further hybridization with a second oligonucleotide to a branched DNA, which in turn hybridizes with a multitude of oligonucleotides coupled with a signal-producing enzyme. The attachment of a great amount of signal-producing enzyme units per existing target molecule is possible thanks to the branching of the DNA.

In a further embodiment of the method according to the invention the sample material is contacted with a T1-specific antibody or fragments of such an antibody. Suitable antibody fragments are e.g. Fab- and F(ab)₂ fragments. The antibodies or antibody fragments can e.g. directly be incubated with the tissue section or, however, be exposed to an immunoassay in which protein extract is e.g. fixed to microtiter plates, separated on a gel matrix or made accessible to the antibody in another way or brought into contact therewith. The antibodies may be monoclonal or polycolonal antibodies; they may e.g. be mouse, rabbit or rat antibodies. The antibodies should specifically react with the T1 protein or selected epitopes of said protein. In one embodiment the method is carried out with antibodies which are specific for the p9 peptide or the p16 peptide of mouse T1 (Werenskiold, 1992). The p9 peptide derives from a region which covers a complete immunoglobulin-similar semidomain of the protein. The p16 peptide corresponds to the carboxy-terminal part of the protein and contains no sequence related to the lgC2 motif of the immunoglobulin superfamily. The antibodies can be directed against the p9 or p16 peptide of the mouse or corresponding peptides of other mammals provided that they cross-react with the corresponding T1 protein of human origin.

In a preferred embodiment the antibodies are directed against antigenic determinants of the human soluble T1 protein. To minimize the risk of a cross reaction with complete membrane-bound receptor, a peptide should be selected which is not present in the T1 receptor. In a preferred embodiment the antibody is directed against a peptide which comprises the sequence p-SKEC (SEQ ID NO:5). The region coding for said peptide is located between the exons 8 and 9 and is only expressed for the soluble protein (T1-S), but not for the receptor (T1-M).

According to the invention there is further provided a kit which is suitable for performing the method according to the invention. The kit contains T1-specific antibody or fragments thereof and optionally means for detecting the antibody or the fragments thereof. These means may for example be enzyme-conjugated anti-lg antibodies which specifically bind to the anti-T1 antibodies respectively used. Said antibodies may be detected with the standard methods that have already been discussed above. The means required therefor, e.g. enzyme substrate, may also be provided in the kit. Furthermore, the kit may be constructed such that the antibodies or antibody fragments which are suitable for detection are present in coupled form with the solid phase. The solid phase may e.g. have the form of microparticles, such as glass, polyacrylamide or Sephadex beads, or consist of microtiter plates. Other possibilities of fixing the antibodies to a solid matrix are also included.

The antibody (or fragments thereof) which is provided in the kit according to the invention may be a monoclonal or polyclonal antibody. Said antibody is produced in a manner known to the person skilled in the art by immunization with the respectively desired antigen, i.e. the p9 or p16 peptide. Sufficient amounts of said peptides can be provided by recombinant expression in eukaryotic systems, e.g. in the vaccinia virus system (Werenskiold, 1992) or in prokaryotic hosts, e.g. in E. coli, B. subtilis or streptomycetes. Instead of natural or recombinantly expressed proteins, synthetically produced peptides are used for immunization in a further embodiment. Particularly preferred are peptides which comprise the sequence p-SEKC (SEQ ID NO:5).

As has already been mentioned, the nucleotide sequence of the T1 gene and thus the coding region of the T1-mRNA are known. Being aware of the sequence, one skilled in the art can readily select suitable primers. Preferred embodiments provide for the use of an oligonucleotide with the sequence 5'-CTT TGA TCA CCT GAA CTT TCT CTA GCA-3' (SEQ ID NO:1) as the first oligonucleotide and that of an oligonucleotide with the sequence 5'-AGT TTT CGG TTG TTG GTG CAT TTC-3' (SEQ ID NO:2) as the further oligonucleotide. In preferred embodiments at least one of the oligonucleotides is conjugated at its 5' end with an antigen or an enzyme capable of producing a signal.

In a further embodiment a kit is provided which is suitable for detecting T1-specific nucleic acids, preferably T1-specific mRNA. The kit contains at least one oligonucleotide which is complementary to T1-mRNA and can thus hybridize therewith and optionally serve as a primer for reverse transcription and/or polymerase chain reaction. Kits which are to serve the performance of a PCR in the end may further contain one or a plurality of further oligonucleotides which correspond to the sense strand of the T1-mRNA and allow for the amplification of the T1-mRNA in combination with the first oligonucleotide.

Moreover, an inventive kit for detecting the T1-mRNA may further contain the enzymes required for the reverse transcription and/or amplification, e.g. reverse transcriptase, DNA polymerase, RNase H, T7 polymerase and/or means for detecting the amplified products. The amplification products can e.g. be detected by incorporated modified nucleotides, for example digoxigenated or biotinylated nucleotides, or however by hybridization of an oligonucleotide which is or can be labeled and is complementary to the T1-mRNA or the complementary strand thereof. A further possibility of detection lies in the use of modified primers which are e.g. connected at their 5' end to an antigen which is recognized by an enzyme-bound antibody. The literature gives innumerable examples of such methods of detection, which are known to one skilled in the art and determine the design of the kit in detail.

As has already been mentioned, the nucleotide sequence of the T1 gene and thus the coding region of the T1-mRNA are known. Being aware of the sequence, one skilled in the art can readily select suitable primers. Preferred embodiments provide for the use of an oligonucleotide with the sequence 5'-CTT TGA TCA CCT GAA CTT TCT CTA GCA-3' as the first oligonucleotide and that of an oligonucleotide with the sequence 5'-AGT TTT CGG TTG TTG GTG CAT TTC-3' as the further oligonucleotide. In preferred embodiments at least one of the oligonucleotides is conjugated at its 5' end with an antigen or an enzyme capable of producing a signal.

Furthermore, the present invention relates to the use of T1-specific antibodies or fragments of such antibodies for detecting the presence of T1 protein in tissue samples, blood or serum samples of a patient with carcinoma of the breast. The T1 protein can be detected with the method of the invention. The invention also relates to the use of T1-specific oligonucleotides for detecting T1-mRNA in sample material of patients with carcinoma of the breast. The oligonucleotide used may be a sense or antisense oligonucleotide.

The figures and the following examples will explain the invention.

BRIEF DESCRIPTION OF THE SEVERAL VIEWS OF THE DRAWING

FIG. 1 comprises FIGS. 1A, 1B and 1C that are images of gels relating to the detection of human T1-mRNA species in cultivated cells and in primary tissue. Total RNA (10 µg, lanes 1, 3, 5) or poly(A)⁺-RNA (1 µg, lanes 2, 4) of established keratinocytes of the skin (Ha-Cat, lanes 1, 2) and mast cells (HMC-1, lanes 3, 4) and of mature placenta (5) were fractionated with a 1% agarose gel, transferred to a nylon membrane and hybridized with T1-specific samples.

Quantitative evaluation: densitometric determination of the ethidium bromide intensity of the specific amplificates of the actin- and T1-mRNA. The T1-mRNA expression observed was evaluated as follows:

signal intensity T1: actin<0.1: T1-negative, Class I signal intensity T1: actin=0.1 to 1: T1-positive, Class II signal intensity T1: actin>1: T1-positive, Class III FIG. 3 is a graph showing the probability, in percent, of relapse-free survival vs. the number of months for metastasis in nodal-negative patients. The probability of a relapse-free survival was determined for the group of 16 nodal-negative patients of Example 4. Plotted is the number of surviving patients in dependence upon time and subdivided according to patients whose breast carcinoma cells were T1-negative (n 8, 0 relapses) or T1-positive (n=8, 5 relapses).

Figure 4A:
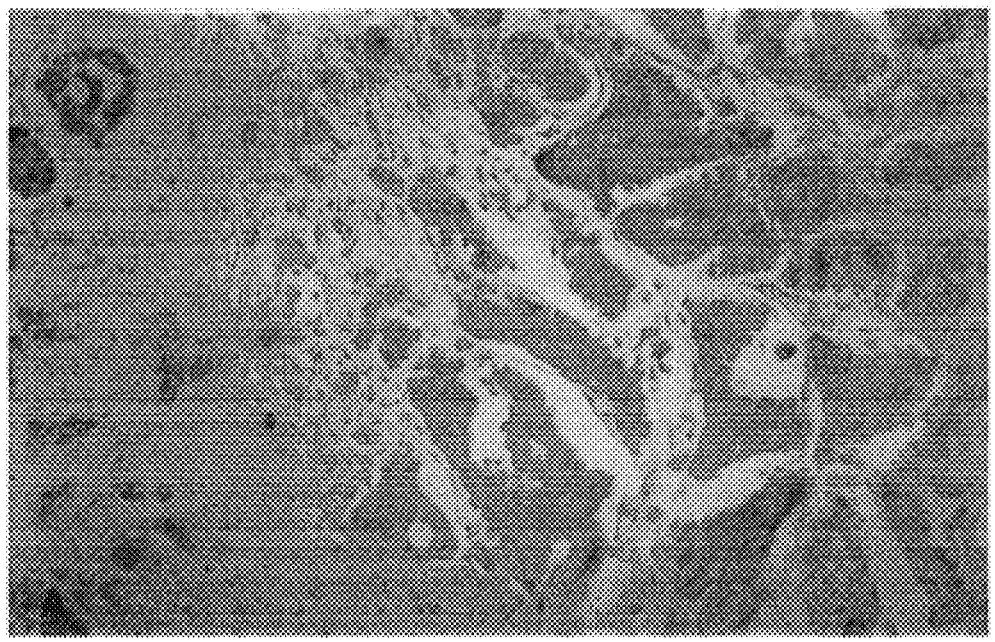
Figure 4B:
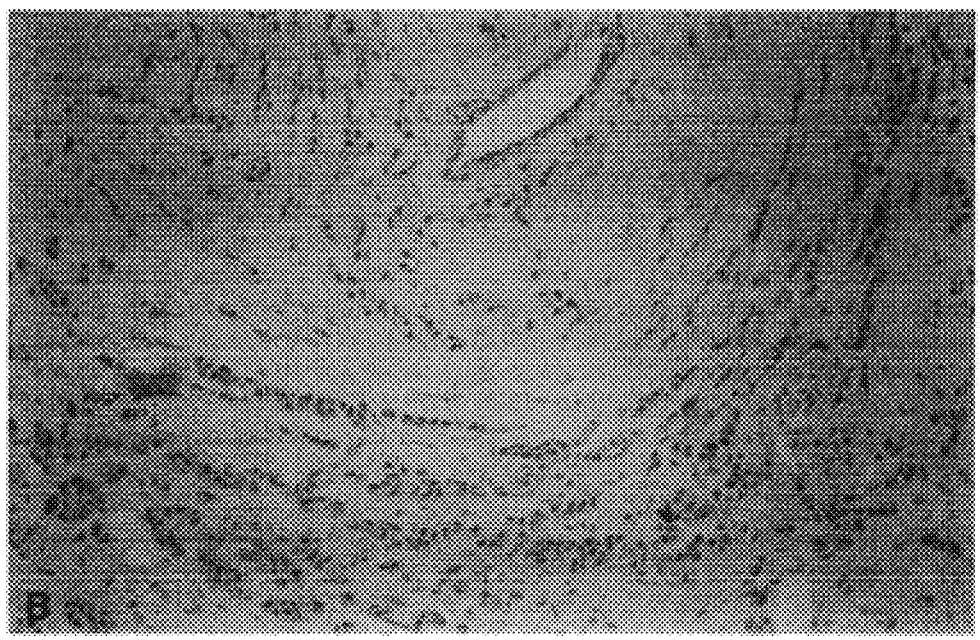

FIG. 4 comprises FIGS. 4A and 4B that are images relating to the detection of T1 protein in carcinomas of the breast. Immunostaining was performed as indicated in Example 5.

FIG. 4A depicts a tissue section showing ductal carcinoma. FIG. 4B depicts a tissue section showing ductolobular carcinoma.

T1-specific signals (dark staining) can only be observed in tumor cells, but not in surrounding stroma.

FIG. 5 is a graph relating to the prognostic importance of the T1-S-RNA level to the illness development of patients with nodal-negative carcinoma of the breast. The T1-RNA level was determined for a group of 55 cases (Examples 6, 10). Plotted is the probability of a relapse-free survival within a follow-up period of 5 years. The illness developments of patients whose carcinoma of the breast showed a low T1-RNA level (n=21, 7 relapses) or a high T1-RNA level (n=34, 3 relapses), respectively, were plotted separately.

EXAMPLES

Material and Methods

1. RNA Preparation 1.1 For the isolation of total RNA from deep-frozen tumor tissue the tissue was first pulverized under liquid nitrogen in an RNase-free mortar. 1 ml Gua-SCN solution (4 M guanidinium isothiocyanate, 25 mM sodium citrate, pH 7.0, 0.5% sodium lauroyl sarcosinate, 0.1 M β-mercaptoethanol) was respectively pipetted to 100 mg of the pulverized mixture. The suspension was transferred into an Eppendorf reaction vessel (ERG). 90 µl 2 M Na-acetate pH 4.0 (1/10 vol.), 900 µl aqueous phenol and 180 µl chloroform/isoamyl alcohol (49:1; v:v) were successively pipetted to said suspension with thorough mixing after each step. Incubation was then carried out on ice for 15 min and at room temperature for 10 min and centrifugation was subsequently performed at 10000×g for 10 min.

The aqueous phase was carefully lifted and transferred into a new ERG. The RNA was precipitated with 900 µl isopropanol (1 vol.) at −20° C. (>1 hour).

Cleaning:

As soon as the RNA was present in a precipitated form, attention was paid to RNase-free working (RNA solution was always cooled on ice; only freshly autoclaved water was used; the wearing of gloves was compulsory).

An additional ethanol precipitation was carried out for cleaning the RNA: The isopropanol-precipitated RNA was pelleted (4° C., 10000 g; 10 min) and washed with 70% ethanol. The pellet was completely dissolved in 300 µl $H_2O$bidest and then mixed with 1/10 vol. Na-acetate (see above) and 900 µl (3 vol.) ice-cold ethanol$_{(absolute)}$. The RNA was again precipitated overnight at −20° C. After centrifugation at 4° C. (20 min; 10000×g) the pellet was washed with 70% ethanol, dried and received in 20–50 µl $H_2O$bidest The RNA was stored either at −70° C. or in ethanol at −20° C.

1.2 Poly(A)$^+$-RNA was enriched by using poly(A) quick columns (Stratagene, Heidelberg, Germany) or isolated by chromatography on oligo(dT) cellulose, as described in Maniatis, T., et al., 1982, *Molecular Cloning: A Laboratory Manual*; Cold Spring Harbor, N.Y.

2. Northern Blots

For Northern blotting 5 µg RNA were first glyoxylated and separated on a 1% agarose gel (McMaster et al., 1977). The gels were stained with acridine orange prior to being transferred to Biodyne membranes (Pall Ultrafine Filtration Co., Glen Cove N.Y.). The RNA was then fixed to the membrane by baking at 80° C. for one hour.

RNA blots were preincubated in hybridizaton buffer (50% formamide, 10 mM Tris hydrochloride pH 7.5, 2×SSC (20×SSC; 3 M NaCl+0.3 M sodium citrate), 5×DenhardT's solution (50×Denhardt's solution): 1% Ficoll, 1% polyvinyl pyrrolidone, 1% bovine serum albumin), 1% sodium dodecyl sulfate and 0.1 mg denatured DNA per ml) for at least 3 hours. Subsequently, they were hybridized in fresh buffer, containing $0.5×10^6$ to $2×10^6$ cpm radio-labeled probe per ml, in a rolling oven (Bachhofer) at 45° C. for 15 hours to 3 days. The filters were thoroughly washed in 0.1×SSC, 0.1% SDS at 65° C. and autoradiographed.

3. PCR Reaction 3.1 Qualitative PCR

For performing the PCR 1 µg of total RNA was denatured at 95° C. for 5 minutes, received in 20 µl RT-PCR buffer (50 mM KCl, 20 mM Tris, 2.5 mM $MgCl_2$, 0.1 mg/ml bovine serum albumin, 1 mM dATP, dCTP, dGTP and TTP pH 8.4, 0.5 units RNasin, 0.09 $OD_{260}$ units of random primer (BRL, Eggenstein, Germany)) and had added thereto 200 units of Moloney murine leukemia virus (MMLV) reverse transcriptase (BRL). The reaction batches were incubated at 20° C. for 10 minutes and then at 42° C. for 45 minutes, and the reaction was then concluded by heating to 95° C. for 5 minutes. The cyclic reactions were carried out in a thermal cycler (TC1, Perkin Elmer, Überlingen, Germany) for amplification purposes. Each cycle consisted of denaturation at 94° C. for 1 minute, hybridization at 55° C. for 1 minute and polymerization at 72° C. for 3 minutes. 30 amplification cycles were performed. The polymerization was prolonged by 10 minutes in the last cycle.

In each amplification test a 10 μl aliquot of the reverse transcription cocktail was used. The aliquots were incubated at a total volume of 50 μl in RT-PCR buffer containing 10 pmol of each of the two specific primers and 1 unit of DNA polymerase (AmpliTaq, Perkin Elmer). After completion of the reaction the samples were extracted with chloroform and the reaction products were observed after separation of the aliquots of the reaction on 2% agarose gels.

3.2 Semiquantitative PCR (for Examples 1 and 2)

For the semiquantitative PCR analysis, parallel batches are used with different cDNA dilutions (corresponding to 500 ng/125 ng/31 ng total RNA) for the T1-PCR reaction (50 μl). 2 μl are removed from the already pipetted, but not yet amplified reaction mixture and amplified in a separate 50 μl batch together with 10 pm actin primer under the same conditions as described for the qualitative PCR. The primers used for the amplification reaction flanked a 322-bp fragment of the T1-S3'NTR (T13'seq and T13'rev) or a 650-bp fragment of the sequence (Acseq and Acrev) coding for human actin. The primers had the following sequences:

T13'seq: CTTTGATCACCTGAACTTTCTCTAGCA (SEQ ID NO:1)

T13'rev: AGTTTTCGGTTGGTGCATTTC (SEQ ID NO:2)

Acseq: GGTCACCCACACTGTGCCCATCTA (SEQ ID NO:3)

Acrev: GCATTGCGGTGGACGATGGAGGG (SEQ ID NO:4)

Identical amounts of the amplified T1 batches and the actin reactions are subjected to electrophoresis on 2% agarose gels for the purpose of evaluation. The ratio of the band intensities of the T1- and actin-specific bands is determined by densitometry.

3.3 Semiquantitative RT-PCR (for Example 6)

The reverse transcription and the PCR analysis were substantially carried out as described under 3.2, but a PTC100 Thermocycler (Biozym, Oberldorf, FRG) was used. The batches were subjected to 30 amplification cycles, each cycle comprising 30 seconds at 92° C., 1 minute at 55° C. and 1 minute at 72° C.

The primers described under 3.2 were used. For the semiquantitative analysis reverse transcripts of 25 to 250 ng RNA were used as the template for the PCR amplification of T1-S in an end volume of 25 μl. 1 μl of the T1-PCR batches, which were completely pipetted together, served as a template for the amplification of actin in a separate tube in an end volume of 25 μl. The corresponding T1-S- and actin-specific PCR reactions were amplified at the same time. 10 μl of the reaction products were mixed and separated in 1.5% agarose gels (70 min, 4 V-CM). The gels were stained with ethidium bromide and the ethidium bromide fluorescence was recorded using a gel print 2000 i video documentation system (MWG Biotech, Ebersberg, FRG). The signal intensity was quantified using the integrated 1 D Scan Software. After normalization of the T1-S-specific signals the T1-S-MRNA expression levels were calculated on the basis of the actin-specific signals of the corresponding PCR reaction. Samples without the addition of an RNA template in all reverse transcription reactions and PCR batches were used as a negative control. Placenta RNA was used as an external standard for the reverse transcription and PCR amplification and yielded a T1-RNA level of 1.8±0.1. Dilution series of the cDNA were analyzed in each PCR. The T1 levels calculated from different dilutions normally differed by less than 10%. The average T1 levels for the individual tumor RNA samples were calculated on the basis of at least two independent PCR runs (with at least 2 dilutions of the cDNA) for each of the two independent reverse transcription reactions. The quantitative resolution of the method is here demonstrated in a dilution experiment: T1-positive placenta RNA was diluted in a dilution series in the ratio of 1:3 with T1-negative RNA from BeWo chorionic carcinoma cells. 25 ng of each RNA mixture were used as a template for RT-PCR. The batches which contained a decreasing amount of placenta RNA (25 to 0.8 ng) yielded decreasing amounts of the T1-specific amplification product in the presence of a constant amount of actin-specific products in all reactions. The plotting of the T1-mRNA level versus the amount of T1-positive placenta-RNA template in each reaction shows a linear correlation over a range of 0.8 to 8.3 ng template. In the presence of 25 ng placenta RNA in the RT-PCR test the T1 amplification exceeded the linear range of the test.

4. In-situ Hybridization 4.1 Immunohistochemical Method for Example 2

Frozen sections from frozen tumor tissue of a thickness of 7 to 9 μm were cut at −20° C., transferred to silane-coated slides and fixed in 4% paraformaldehyde (PAF) in phosphate-buffered saline solution (PBS) (137 mM NaCl, 2.7 mM KCl, 4.3 mM disodium hydrogen phosphate, 1.4 mM potassium dihydrogen phosphate, pH 7.3) for 30 minutes. Fixed sections were dried at 43° C. Prior to hybridization the sections were rehydrated in PBS at room temperature for 5 minutes, treated with proteinase K (2 μg/ml in 100 mM Tris, 5 mM EDTA, pH 8) at 37° C. for 5 to 10 minutes and refixed in 4% PAF in PBS at room temperature for 5 minutes. The samples were subsequently washed in PBS for 3×3 minutes and incubated for 10 minutes under dropwise addition of 0.25% acetic acid anhydride in 100 mM triethanol amine. The sections were prehybridized in 50% formamide, 2×SSC (0.3 M NaCl, 30 mM sodium citrate, pH 7) at 37° C. for at least 1 hour.

Subsequently, each frozen section had added thereto 20 μl hybridization buffer (50% formamide, 2×SSC, 10% dextrane sulfate, 0.1% SDS, 250 μg/ml denatured salmon-sperm DNA, pH 7) containing 1×10$^6$ cpm $^{35}$S-labeled RNA probe, and hybridization was carried out in a moist-chamber culture dish at 42° C. for 16 to 18 hours. The sections were washed in 4×SSC at 42° C. three times for 20 minutes, treated with RNase A (20 μg/ml in 0.5 M NaCl, 10 mM Tris, 5 mM EDTA, pH 8) at 37° C. for 30 minutes, washed once with 2×SSC and once with 1×SSC at 42° C. for 30 minutes, dehydrated in ethanol and air-dried. The dry slides were immersed into Kodak NTB-2 photoemulsion (Tecnomara, Femwald), exposed for 1 to 3 weeks, then developed (Kodak D 19) and fixed (Unifix, Kodak). Subsequently, the sections were stained with hematoxylin and eosin, dehydrated, embedded in Eukitt (Kindler, Freiburg, Germany) and viewed by using a Zeiss axioscope with light/dark field means.

4.2 Immunohistochemical Methods for Examples 7 and 8

The polyclonal serum which was produced against a synthetic peptide corresponding to the C-terminal sequence of mouse T1-S has already been described (Rössler, 1995b). Purified IgG was used at a concentration of 7 μg/ml. The monoclonal antibody M144 was produced in rats against recombinant human T1-S-Fc from COS cells; the working concentration was 16 μg/ml. The immunohistochemical studies were carried out on formalin-fixed paraffin-embedded sections using the ABC vector-peroxidase staining kit (Camon, Wiesbaden, FRG). The specificity of the T1 staining was confirmed by preadsorption with a 25-times molar excess of purified antigen prior to immunostaining by using irrelevant control antibodies. No signals were obtained in these reactions. Moreover, both T1-specific antisera reacted with T1-mRNA-positive, but not with T1-mRNA-negative cultivated cells under the test conditions used for staining the tumor sections.

The immunohistochemical T1-reactivity was determined by modifying the method described in Remmele and Stegler, 1987, using two multiplicators: The T1 staining intensity was classified as non-existing (0), low (1), average (2) or high (3). The classification of the percentage of T1-reactive tumor cells was carded out with the following cut-off limits: ≧80% (4), ≧50% (3), ≧20% (2), ≦20% (1), 0% (0). The T1-protein level was obtained as the product of the two variables and covered a range of 0 to 12.

5. Statistical Methods

Univariate analyses were performed by means of Fisher's T test and the chi-square test.

Example 1

Expression of T1-mRNA in Human Cells and Tissues

Figure 1A:
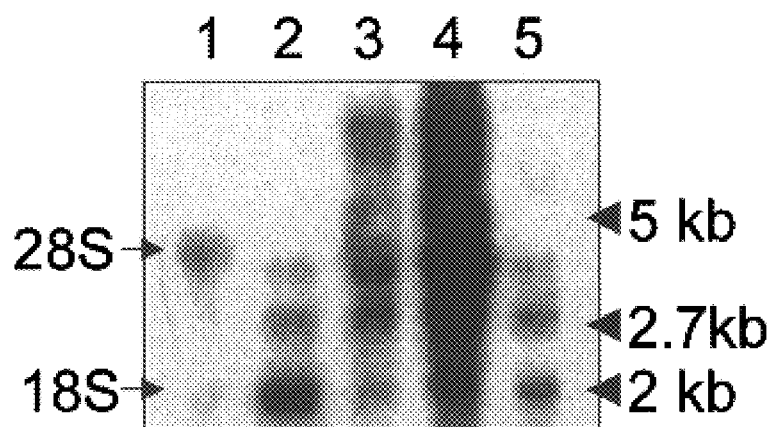
FIG. 1A: Hybridization sample from the ORF (positions 45–602 of the cDNA sequence according to Tominaga, 1992), 3 mRNA species with sizes of 5 kb, 2.7 kb and 2 kb are detected.
Figure 1B:
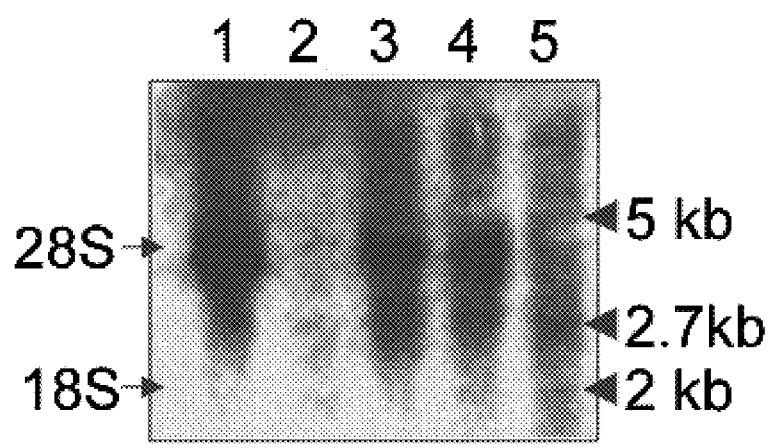
FIG. 1B: Hybridization sample from the 3'-untranslated region (position 990–1310 of the cDNA sequence according to Tominaga, 1992); specifically detects the 2.7-kb T1-mRNA (and unspecifically 28 S rRNA in total RNA samples). The position of the ribosomal RNA (28 S and 18 S) is indicated at the left side.

The T1-mRNA expression was analyzed in total RNA and poly(A)$^+$-enriched RNA which had been isolated from continuous keratinocytes (Ha-Cat) and mature placenta. The Northern-blot hybridization with probes containing the 5' part of the open reading frame of the T1-cDNA showed 3 transcripts of 2 kb, 2.7 kb and 5 kb (FIG. 1A). The size of the two last-mentioned transcripts corresponds fairly well to results obtained in mouse cells in which a T1-mRNA of 5 kb encodes the transmembrane receptor T1-M, and a T1-mRNA of 2.7 kb encodes the tumor-associated soluble T1 protein. Hybridization with a fragment of the 3'-non-translated region (positions 45–602 of the cDNA sequence according to Tominaga, 1992) of the human T1-cDNA confirmed the identity of the human 2.7 kb mRNA with that of the species coding for the excreted T1 protein (FIG. 1B).

Figure 1C:
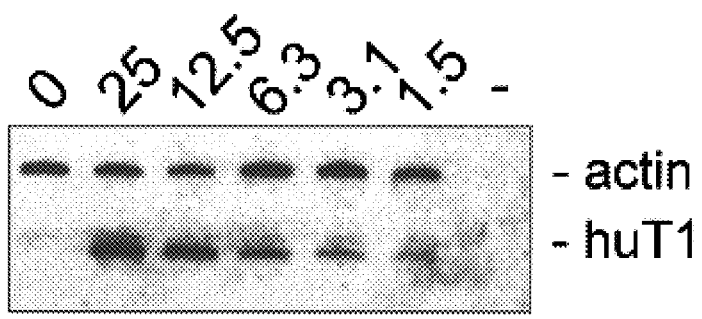
FIG. 1C: Semiquantitative RT-PCR for detecting the 2.7 kb T1-mRNA. T1-positive total RNA from placenta was serially diluted in T1-negative total RNA of the cell line U2OS, and the RNA mixtures were reversely transcribed. Aliquots of the cDNA, each corresponding to 25 ng RNA mixture/test, were analyzed by means of PCR (see material and methods: 25 ng for T1-PCR, 1 µl taken therefrom for actin PCR). The amount of placenta RNA (in ng) per 25 ng total RNA is indicated above the lanes. (Zero: reaction only with T1-negative RNA; minus: negative control, i.e. PCR without cDNA template). 10 µl of the reaction products were respectively separated in a 2% TBE (trisborate/EDTA buffer) gel and stained with ethidium bromide.

For a more sensitive detection of T1-mRNA in tumors a semiquantitative RT-PCR test was established. Specific PCR primers were selected for the excreted tumor-associated T1 variant in such a manner that they led to the production of a 322-bp fragment in the 3'-non-translated region. Actin sequences were coamplified as an internal control. After the RT-PCR of RNA preparations, which had turned out to be positive in Northern blot hybridizations, amplification products of the expected size were obtained. The quantitative resolution of the method was demonstrated in a dilution experiment. A dilution series of T1-positive placenta RNA was prepared in T1-negative RNA of the same concentration and analyzed by means of RT-PCR. As shown in FIG. 1C, a linear decrease in the T1-specific amplification product was observed in reactions containing 25 to 1.5 ng placenta RNA. Constant amounts of actin-specific products were obtained in all reactions because of the presence of increasing amounts of T1-negative RNA.

Example 2

T1-mRNA Expression in Carcinomas of the Breast

The total RNA of freshly frozen tissue of 41 patients with invasive carcinoma of the breast and of 6 patients with mastopathy was isolated; placenta was used as a positive control tissue. The expression of the 2.7 kb T1-mRNA was examined by means of the above-described semiquantitative RT-PCR.

Figure 2:
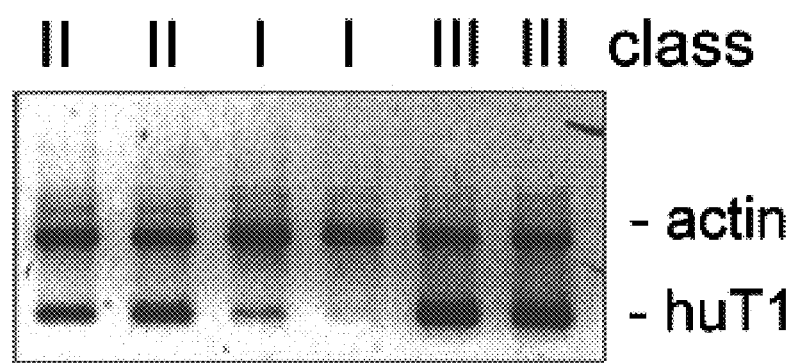
FIG. 2 is an image of a gel relating to the use of semiquantitative RT-PCR for detecting 2.7-kb T1-mRNA in total RNA from carcinomas of the breast. Performance, see material and methods. 10 µl of the reaction products were respectively separated on agarose gels and stained with ethidium bromide.

The coamplified actin sequences from the same sample were used as internal standard for the quantitative evaluation of the T1 expression (see FIG. 2).

In all of the 6 samples of mastopathy patients no T1-mRNA or only negligibly small amounts were detected.

By contrast, the T1-mRNA levels in RNA obtained from tumor tissue showed a high variability. The quantitative evaluation was made by densitometry (see legend regarding FIG. 2). A classification scheme with 3 categories was used for the further analysis. The T1 mRNA levels were evaluated as follows:

(I): T1-negative: T1 amplificaton product not detectable or only very weakly visible (T1: actin<0.1);

(II) T1-positive: average T1-mRNA values, clearly detectable, but weaker than the actin signal.(T1: actin= 0.1 to 1);

(III): T1-positive: high T1-mRNA values, signal equally strong or stronger than the actin signal (T1: actin>1).

Examples of the evaluation pattern are shown in FIG. 2. Upon application of this scheme Class (I) comprised all of the 6 mastopathy samples and 34% of the tumors (N=13). 49% of the tumors (N=21) were evaluated as Class (II) and 17% of the tumors (N=7) showed high T1-mRNA levels of Class (III) (see Table 2).

Example 3

Correlation of the T1 Expression with Known Prognosis Criteria 3.1 T1 Expression and Histological Type Of the 40 carcinomas analyzed, 12 were lobular carcinomas, 7 ductolobular ones and 21 ductal carcinomas. The following T1 expression was detected in said tumors:

TABLE 2

| Histological type | T1-mRNA level | | |
|---|---|---|---|
| | I | II | III |
| lobular (12) | 5 (42%) | 5 (42%) | 2 (16%) |
| ductolobular (7) | 1 (14%) | 6 (86%) | — |
| ductal 21 | 6 (28%) | 10 (48%) | 5 (24%) |

3.2 T1 Expression and Tumor Grading

The T1 expression showed no correlation with tumor grading.

3.3 T1 Expression and Tumor Size

T1 expression and tumor size correlate as follows:

TABLE 3

| Tumor size | T1-mRNA level | | |
|---|---|---|---|
| | I | II | III |
| pT1 (15) | 9 (60%) | 5 (33%) | 1 (7%) |
| pT2 (17) | 2 (12%) | 10 (59%) | 5 (29%) |
| p T3/p T4 (9) | 3 (33%) | 5 (56%) | 1 (11%) |

3.4 T1 Expression and Nodal State

The following relations were observed between T1 expression and nodal state:

TABLE 4

| Nodal state | T1-mRNA level | | |
|---|---|---|---|
| | I | II | II |
| nodal-negative (22) | 9 (41%) | 10 (45%) | 3 (14%) |
| nodal-positive (16) | 5 (31%) | 9(56%) | 2 (13%) |

Example 4
Prognostic Significance of the T1-mRNA Expression

4.1 Proanostic Significance for All Patients

Of 32 patients observed, 24 patients (75%) survived the observation period of 47 months. Within said period carcinomas reappeared in 16 of the patients observed (50%). In a univariate analysis of all patients the T1 measurement did not allow for any predictions regarding relapses or survivals. By contrast, the classical prognosis factors, lymph node state and tumor size, had a highly prognostic value.

4.2 Prognostic Significance of the T1-mRNA Expression in Axillary Nodal-negative Patients The nodal-negative group comprised 18 patients, of whom 7 (39%) developed a renewed carcinoma. In the nodal-negative group of patients the degree of the T1 expression was a strongly prognostic indicator of a recurrence of the disease, comparable with the known Ki67 marker, whereas the tumor size turned out to be of no value from a prognostic point of view. None of the 8 nodal-negative, T1-positive patients developed a recurring disease within the period of observation. In 2 additional patients of said group bone metastases were already diagnosed at the time of surgery, both survived during the period of observation. By contrast 5 out of 8 nodal-negative, T1-negative patients (62.5%) developed a recurring carcinoma and 2 (25%) died within the period of observation (see FIG. 3).

4.3 Prognostic Significance of the T1-mRNA Expression in Axillary Nodal-positive Patients The group of nodal-positive patients comprised 14 patients, of whom 9 developed a recurrent carcimona. Of these, only 4 were T1-negative. Metastases were diagnosed in one patent at the time of surgery. The 3 nodal-negative patients without metastases remained carcinoma-free. Of the 10 nodal-positive, T1-positive patients, 8 (80%) developed a recurrent carcinoma and 6 (60%) died within the period of observation.

Example 5
Immunohistochemical Analysis of Carcinoma Samples of the Breast

Tissue sections of formalin-fixed, paraffin-bedded tissue at a thickness of 5 $\mu$m were deparaffined and incubated with a polyclonal antiserum against the carboxy-terminal sequence of T1 (Rössler, 1995a) (8.5 $\mu$g IgG/ml). The T1-specific immunoreaction was detected by means of a secondary biotinylated anti-rabbit antibody, an avidin-peroxidase complex and diamino-benzidine staining (Immunostaining Kit Vectastain Elite ABC Kit, Vector Laboratories via SERVA, Heidelberg, FRG). T1-specific staining: brown, counterstaining with hematoxylin: blue. The analysis furnishes proof of the presence of T1 protein in tumor cells, but not in the surrounding stroma (FIG. 4). The results of the immunohistochemical analysis therefore correspond to those of the in-situ hybridization with T1-specific probes.

Example 6
T1 S-mRNA Level and Progression of the Illness Development of Axillary Nodal-negative Patients In a later study the level of tumor-associated T1-S-mRNA was analyzed in the tissue of 55 patients with primary invasive nodal-negative breast cancer and 6 cases of FCD (fibrocystic dysplasia without atypism; a benign, fibrotic change in the breast). All of the patients were subjected to mastectomy in the hospital of the Technical University of Munich between 1989 and 1993 and selected for the study because freshly frozen tissue and clinicopathological data were available from said patients. The clinical data of the patients are summarized in the following Table 5.

TABLE 5

Clinical data of the group of patients:

|  |  |  | T1-RNA level | |
|---|---|---|---|---|
| Parameter | Definition | N = (55) | low (21) | high (34) |
| Tumor size | <3 cm | 33 | 13 | 20 |
|  | >3 cm | 22 | 8 | 14 |
| Average age | Years | 55 | 52 | 59 |
| Estrogen | ER-negative | 10 | 4 | 6 |
| receptor (ER) | ER-positive | 45 | 17 | 28 |
| Progesterone | PR-negative | 20 | 9 | 8 |
| receptor (PR) | PR-positive | 35 | 12 | 26 |
| Tumor state p = | G < 3 | 34 | 9 | 25 |
| 0.0224 | G3 | 21 | 12 | 9 |
| Relapses p = | Relapses | 10 | 7 | 3 |
| 0.0220 | No relapses | 45 | 14 | 31 |
| Tumor-induced | died | 6 | 3 | 3 |
| deaths | alive* | 49 | 18 | 31 |

*at the date of the follow-up examination

The T1 S-mRNA levels in the breast tissue were determined in the total RNA by using the above-described sensitive semiquantitative RT-PCR test (see material and methods, 3.3) by which the 3'-non-translated region of the T1-S-mRNA is detected. Normalized T1-RNA levels were calculated on the basis of the tumor-associated T1-S-mRNA levels and classified as low (T1 level≦0.1) or high (T1 level≧0.1). The 6 FCD cases and 21 of the 55 breast cancer cases (38%) showed a low T1-RNA level. Of the 34 (62%) tumors with a high T1-RNA level, 26 (47%) showed an average level (T1-RNA level≦0.5) while 8 (15%) tumors contained high levels (T1-RNA levels≧0.5) of T1-S-mRNA.

The correlation of the T1-RNA level with different clinicopathological parameters was examined in a univariate analysis; the results are summarized in Table 5. The T1-RNA levels revealed no correlation with the age of the patient, the histological tumor type, the tumor size or the expression of estrogen and/or progesterone receptors. The T1-RNA level, however, was significantly associated with the tumor differentiation (p=0.022): 25 out of 34 (70%) of the tumors having a high T1-RNA level, but only 9 out of 21 (43%) of the tumors with a low T1-RNA level were differentiated to a good or moderate degree (G1, G2). Furthermore, the T1-RNA level was significantly associated with the disease-free survival of the patients within an average period of observation of 5 years (37 to 93 months): 10 out of 55 patients (18%) became ill again. There were relapses in 7 of 21 (33%) of the tumors having a low T1-RNA level, but only in 3 of 34 (9%) tumors having a high T1-RNA level. 91% of the cases with a high T1-RNA level stayed healthy. This group with an excellent prognosis comprised all of the 8 patients with the highest T1-RNA level (≧0.5). As a consequence of the small number of patients, such a detection was not significant from a statistical point of view. The risk of a later recurrence of the disease was 3.7 times smaller in tumors with a high T1-RNA level than in tumors having a low T1-RNA level (p=0.022). Kaplan-Meyer curves for the disease-free survival of the patients with a high versus low tumor-associated T1-RNA level revealed a significant difference within a period of observation lasting for 17 months (FIG. 5).

Example 7
Immunohistological Detection of T1 Protein in Breast Cancer Tissue For 31 of the breast carcinomas analyzed in Example 6 by means of RT-PCR, formalin-fixed, paraffin-embedded tissue was available for the immunohistochemical analysis of the T1 protein expression. The antisera used for determining the site of the T1-protein synthesis and the deposition in tumor tissue were (1) a monoclonal antibody which had been produced against human recombinant T1-S protein, and (2) a polyclonal antiserum which specifically reacts with murine T1-S protein, but not with T1-M protein (anti-c peptide; R össler et al., 1995a). The immunohistochemical tests were carried out with two antibodies; both antibodies led to similar results.

Tissue sections of normal breast tissue and FCD tissue revealed a slight T1 reactivity in the ductal epithelial cells. Of the 31 analyzed primary breast carcinomas, 30 exhibited a T1-reactivity in the tumor cells, though to very different degrees. The intensity of the T1 reactivity drastically differed between individual cells within a tumor cell cluster and in the fraction of the T1-reactive tumor cells in the tissue from different patients (10% up to >90%). In ductal carcinomas, tumor cells which grew in solid or tubular regions very often showed a higher T1 reactivity than disseminated individual tumor cells. 6 out of 10 tumors which exhibited a high degree of T1 reactivity in the tumor cells also showed a significant T1 reactivity in the stroma. All of the 5 lobular and 2 of the medullary carcinomas showed a low to mean T1 reactivity of the tumor cells. One tumor did not exhibit any immunohistochemically detetectable T1 reactivity while reacting with other antisera, for instance for detecting estrogen and progesterone receptors.

Example 8
Immunohistochemical Determination of the T1-Protein Level

The immunohistochemical T1 reactivity was determined by means of a modification of the protocol of Remmele and Stegener, 1987, with the fraction of the T1 reactive tumor cells and their staining intensity serving as parameters (see material and methods, 4.2). The resulting classification (T1-protein level) covers a range of 0 (no T1 reactivity) to 12 (high T1 reactivity in $\geq 80\%$ of the tumor cells).

11 of the 21 carcinomas with a low T1-RNA level were assayed immunohistochemically and showed a low T1 reactivity with an average T1-protein level of 2.9 (range: 0 to 6). Of the 34 tumors with a high T1-RNA level, 20 were assayed immunohistochemically. 19 out of 20 showed a T1 reactivity with an average T1-protein level of 7.6 (range: 2 to 12). One tumor did not show any immunohistochemically detectable T1 reactivity (T1-RNA level =0.21).

Example 9
Comparison of the Results of RT-PCR and Immunohistochemical Assay

In the assay described in Example 6 the analysis of the expression of the tumor-associated T1 -S levels was based on the sensitive detection of T1-S-mRNA by means of RT-PCR. It was expected that the T1-S-mRNA levels reflect the T1-S protein synthesis since the exhaustive assaying of murine T1 furnished no information about the posttranscriptional regulation of the T1 gene expression. This assumption is confirmed by a comparison of the results obtained with RT-PCR and after immunohistochemical detection of T1 protein for 31 tumors. Only two of the tumors led to inconsistent results in a comparison of the two methods, which might point to a posttranscriptional or translational regulation mechanism: one tumor showed a high T1-S-mRNA level, but no T1 reactivity. A possible explanation for said discrepancy could be a block of the T1-translation. The other tumors showed low T1-S-mRNA levels and a high cellular T1 reactivity. This discrepancy might be based either on an increased translation activity or an intracellular accumulation of the T1 gene product as a consequence of a secretion defect of the cells.

The consistency of the T1 expression levels after determination with two independent methods confirms the applicability of the batch used therein.

Example 10
Prognostic Value of the T1-RNA Determination in Nodal-negative Patients The classical prognostic factors tumor size and hormone receptor state were of no prognostic value in the group of nodal-negative patients which had been examined according to Examples 6 to 9 and which were characterized by a high amount of smaller ($\leq 3$ cm) and poorly differentiated (G3) tumors with a positive status for estrogen and progesterone receptors. The only other factor that is of significance to the prognosis for the patients is tumor grading (p=0.001), which represented the best prognostic indicator for said group. 9 out of 10 relapses occurred in the 21 poorly diffentiated (G3) tumors (43%). Although a multivariate analysis has not been performed in view of the limited number of patients, the data of the inventors indicate that the T1-RNA level is a further useful marker for identifying patients with G3 tumors who have an increased risk for relapses. To demonstrate said effect, patients with G3 tumors were first classified according to their T1-RNA levels. The resulting group of 12 G3 cases with a low T1-RNA level had a drastically increased risk for a recurrence of the disease (6 relapses, 50%) in comparison with the 9 G3 cases with a high T1-RNA level (2 relapses, 22%). A statistically significant separation (p=0.029) of said G3 subgroups was obtained with the corrected T1 level: in 7 out of 12 G3 cases with a low T1 level (58%), but only in one out of 9 cases with a high T1 level (11%), a recurring carcinoma was observed within the period of observation.

The above results demonstrate that the T1 level, either alone or in combination with tumor grading, is a promising novel prognostic indicator to identify patients with nodal-negative breast cancer who have a considerably increased risk as to a recurrence of the disease. The early identification and a selective accompanying therapy of said high-risk patients may be a promising strategy for improving individual prognoses. Present efforts are concentrating on the establishment of simplified methods for evaluating the tumor-associated T1-S expression. As has been shown in Examples 8 and 9, immunohistochemistry on formalin-fixed, paraffin-embedded tissue is a promising alternative to the RNA analysis. Presently, the prognostic significance of immunohistochemically detected tumor-associated T1 is being examined in a larger group of patients.

Bibliography

Allred, D. C., et al., 1992, Human Pathol. 23, 974–979.
Archer, S. G., et al., 1995, Br. J. Cancer. 72, 1259–1266.
Auer, G., et. al., 1994, Cancer Res. 44, 394–396.
Barnes, D. M., et. al., 1993, Human Pathol. 24, 469–476.
Danescu, J., and Werenskiold, A. K. 1995, FEBS Lett. 367, 89–92.
Domagala, W., et al., 1990, Am. J. Pathol. 137,1059–1064.
Gayle, J. et al., 1996, J. Biol. Chem. 271, 5784–5789.
Graff, J. R., et al., 1995, Cancer Res. 55, 5195–5199.
Hoskins, K., and Weber, B. L., 1995, Curr. Opin. Oncol. 7, 495–499.
Jaenicke, F., et al., 1993, Breast Cancer Res. Treatment 24, 195–208.
Kievits, T., et al., 1991, J. Virol. Methods 35, 273–286.

Klemenz, R., et al., 1989, Proc. Nab. Acad. Sci. USA 86, 5708–5712.
Lipponen, P., et al., 1993, Int J. Cancer. 55, 51–56.
Maniatis, T. et al., 1982, Molecular Cloning: A Laboratory Manual; Cold Spring Harbor, N.Y.
McMaster et al., 1977, G. K., and G. G. Carmichael, PNAS 74, 4835–4838, 1977.
Pachl, C., et al., 1994, J. AIDS?, ?
Rasbridge, S. A., et al., 1993, J. Pathol. 169, 245–250.
Remmele and Stegener, 1987, Frauenarzt 2, 41–43.
Rößler, U., et al., 1993, Oncogene 8, 609–617.
Rößler, U., et al., 1995a, Dev. Biol. 168, 86–97.
Rößler, U., et al., 1995b, E. J. Pathol. 1, file 952–03.
Rupp, B., et al., 1995, Biochem. Biophys. Res. Com. 216, 595–601.
Schmitt, M., Graff, H., and Kindermann, G. (1994) Elsevier, Amsterdam.
Sommers, C. L., et al., 1992, Cancer Res. 52, 5190–5197.
Thomassen, E., et al., Cell Growth Differ. 6, 178–184.
Thompson, E. W., et al., 1991, J. Cell. Physiol. 150, 534–544.
Tominaga, S., et al., 1992, Biochem. Biophys. Acta 1171, 215–218.
Walker, G. T., et al., 1996, Nucleic Acids Research 24, 348–353.
Werenskiold, A. K., 1992, Eur. J. Biochem. 204, 1041–1047.
Werenskiold, A. K., et al., 1989, Mol. Cell. Biol. 9, 5207–5214.
Wilhelm, O., et al., In: Prospects in diagnosis and treatment of breast cancer. Elsevier, Excerpta Medica, 145–156.
Yuan, J., et al., 1992, Br. J. Cancer 65, 461–465.

What is claimed is:

1. A kit suitable for use with an in vitro method selected from the group consisting of prognosticating the illness development of a human patient with carcinoma of the breast and diagnosing carcinoma of the breast, the method comprising detecting human T1 protein in sample material obtained from the patient, the kit comprising a T1-specific antibody or fragment thereof, wherein said fragment is selected from the group consisting of Fab and F(ab)$_2$.

2. The kit of claim 1, wherein said T1-specific antibody is selected from the group consisting of a polyclonal antibody and a monoclonal antibody.

3. The kit of claim 2, wherein said T1-specific antibody is a polyclonal antibody.

4. The kit of claim 1, wherein said T1-specific antibody is directed against p9 protein.

5. The kit of claim 1, wherein said T1-specific antibody is directed against p16 protein.

6. The kit of claim 1, wherein said sample is selected from the group consisting of tumor tissue, blood, and serum.

7. The kit of claim 1, wherein said human T1 protein is detected by contacting said sample material with said T1-specific antibody or fragment thereof.

8. The kit of claim 1, further comprising an antibody that specifically binds to said T1-specific antibody or said fragment thereof for detecting said human T1 protein.

9. The kit of claim 8, wherein said antibody for detecting said human T1 protein comprises an enzyme-conjugated anti-Ig antibody that specifically binds to said T1-specific antibody or said fragment thereof or components of said enzyme-conjugated anti-Ig antibody.

10. The kit of claim 9, wherein said T1-specific antibody or said fragment thereof is in a coupled form with a solid phase.

* * * * *

SEQUENCE LISTING

```
<160> NUMBER OF SEQ ID NOS:  5

<210> SEQ ID NO 1
<211> LENGTH: 27
<212> TYPE: DNA
<213> ORGANISM: Artificial Sequence
<220> FEATURE:
<223> OTHER INFORMATION: Description of Artificial  Sequence:PCR Primer
      for amplifying T1 gene

<400> SEQUENCE: 1
ctttgatcac ctgaactttc tctagca                                              27

<210> SEQ ID NO 2
<211> LENGTH: 21
<212> TYPE: DNA
<213> ORGANISM: Artificial Sequence
<220> FEATURE:
<223> OTHER INFORMATION: Description of Artificial  Sequence:PCR Primer
      for amplifying T1 gene

<400> SEQUENCE: 2
agttttcggt tggtgcattt c                                                    21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial  Sequence:PCR Primer
      for amplification of human actin sequence

<400> SEQUENCE: 3
ggtcacccac actgtgccca tcta                                                 24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial  Sequence:PCR Primer
      for amplification of human actin sequence

<400> SEQUENCE: 4
gcattgcggt ggacgatgga ggg                                                  23

<210> SEQ ID NO 5
<211> LENGTH: 4
```

```
<212> TYPE: PRT
<213> ORGANISM: Artificial Sequence
<220> FEATURE:
<223> OTHER INFORMATION: Description of Artificial  Sequence:Antigenic
      peptide region of human soluble T1 protein

<400> SEQUENCE: 5

Ser Lys Glu Cys
  1
```